US006540730B1

(12) United States Patent
Niedermeyer

(10) Patent No.: US 6,540,730 B1
(45) Date of Patent: Apr. 1, 2003

(54) FRONT OPENING BRIEFS WITH INTEGRAL SUPPORT PANEL

(76) Inventor: William P. Niedermeyer, 1024 Mt. Mary Dr., Green Bay, WI (US) 54311

( * ) Notice: Subject to any disclaimer, the term of this patent is extended or adjusted under 35 U.S.C. 154(b) by 0 days.

(21) Appl. No.: 09/286,355

(22) Filed: Apr. 5, 1999

(51) Int. Cl.[7] .......................... A61F 13/15; A61F 13/20; A61B 9/00; A61B 9/02
(52) U.S. Cl. ............................ 604/385.27; 604/385.03; 604/385.09; 604/385.14; 604/385.71; 604/390; 604/391; 604/397; 604/402; 2/401; 2/405
(58) Field of Search ................................ 604/349, 351, 604/385.03, 385.09, 385.21, 385.24–385.28, 393–395, 397–402, 385.14; 2/400–408; 602/67–73

(56) References Cited

U.S. PATENT DOCUMENTS

| 2,037,060 A | * | 4/1936 | Black ............................ 2/404 |
| 2,321,123 A | * | 6/1943 | Bogart .......................... 2/403 |
| 3,714,946 A | * | 2/1973 | Rudes .......................... 604/398 |
| 4,554,684 A | * | 11/1985 | Cadoret ........................ 2/406 |
| 4,589,877 A | * | 5/1986 | Sivilich .................. 604/385.01 |
| 4,944,733 A | * | 7/1990 | Casale |
| 4,960,414 A | * | 10/1990 | Meyer ......................... 604/394 |
| 5,435,014 A | * | 7/1995 | Moretz et al. |
| 5,669,902 A | * | 9/1997 | Sivilich ....................... 604/397 |
| 5,725,714 A | * | 3/1998 | Fujioka et al. ............... 604/389 |
| 5,795,433 A | * | 8/1998 | Niedermeyer |
| 5,864,890 A | * | 2/1999 | Niedermeyer |
| 6,092,242 A | * | 7/2000 | Niedermeyer |
| 6,240,563 B1 | * | 6/2001 | Niedermeyer .................. 2/400 |

FOREIGN PATENT DOCUMENTS

| NO | 121598 | * | 3/1971 | ................. 604/386 |

* cited by examiner

Primary Examiner—Dennis Ruhl
Assistant Examiner—K. M. Reichle

(57) ABSTRACT

A brief assembly with a full front panel opening and an inner elasticized support panel includes two half width segments superposed in overlapping relationship, with a portion of the overlapped central area between rear portions of the segments bonded to form a unitary rear panel. The other half of the overlap is left unbonded to provide the full opening in the front panel. The outer margin of the opening can be reinforced by enclosure within a V-folded strip. Portions of outer side margins on each segment are removed to form an hourglass-shape. Overlapped segments are held together by a releasable fastener means that joins the two front panel half width segments. Tensioned elastic strands are attached to a support panel at spaced intervals. The support panel is secured to the inner surface of the overlapped segments. Tapes or other fasteners protrude from the side margins and are used to complete the waist and leg apertures after the front half is folded upward around a user's body. The support panel can have release strip covered adhesive receptor areas to accept an absorbent pad insert of the user's choice.

12 Claims, 2 Drawing Sheets

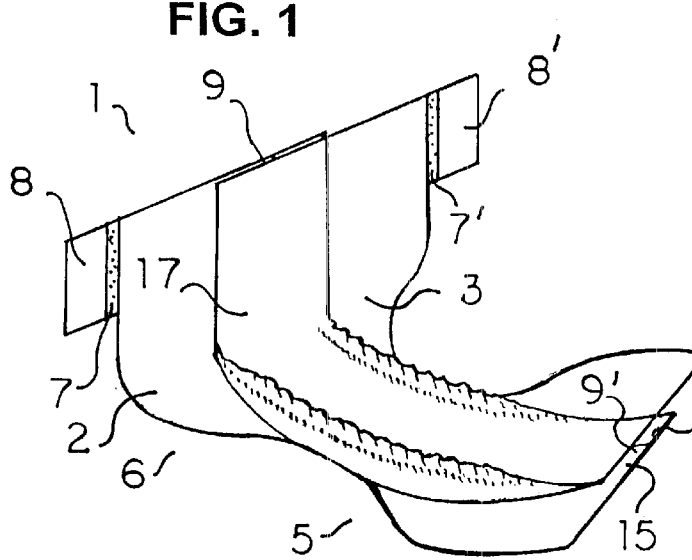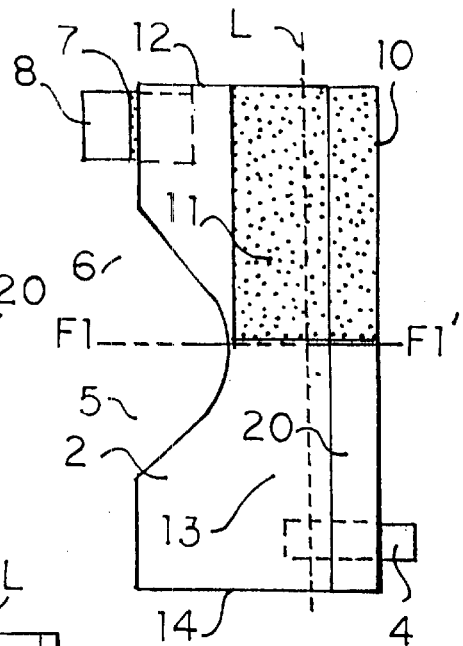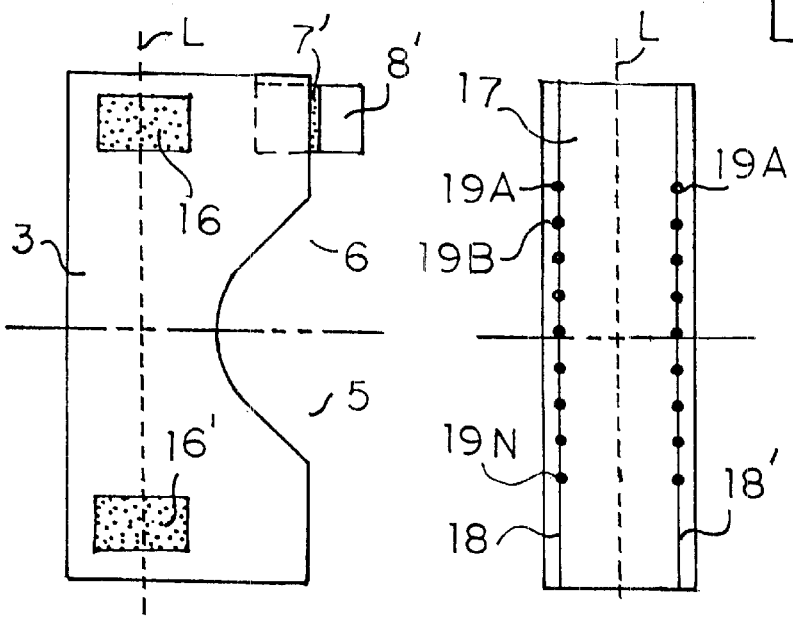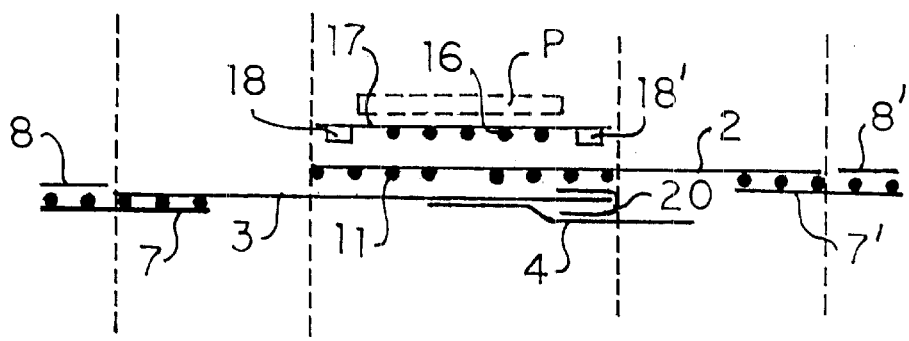

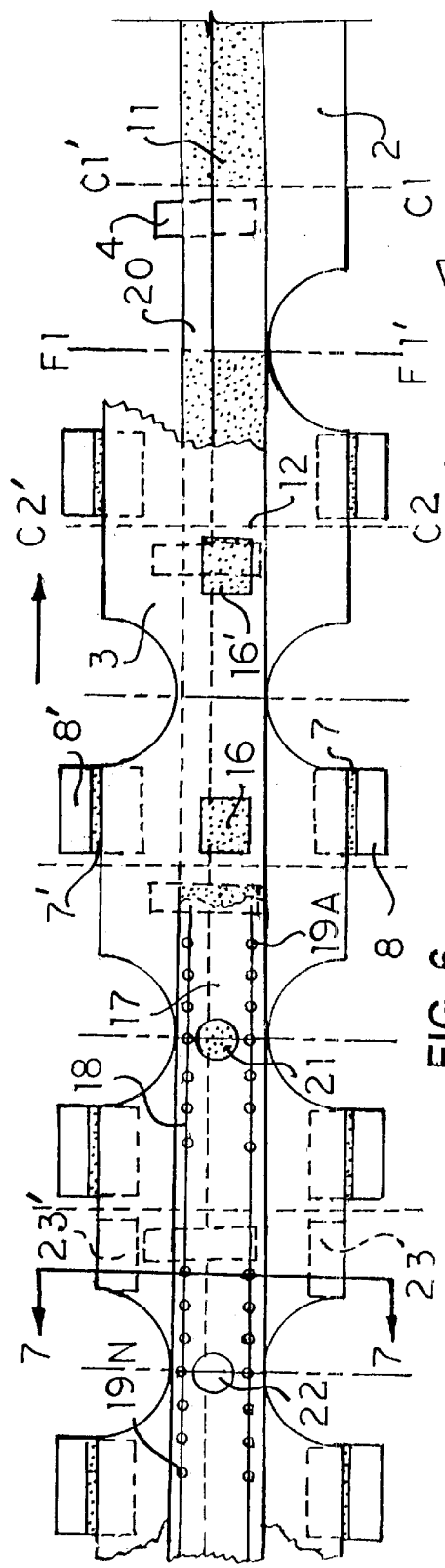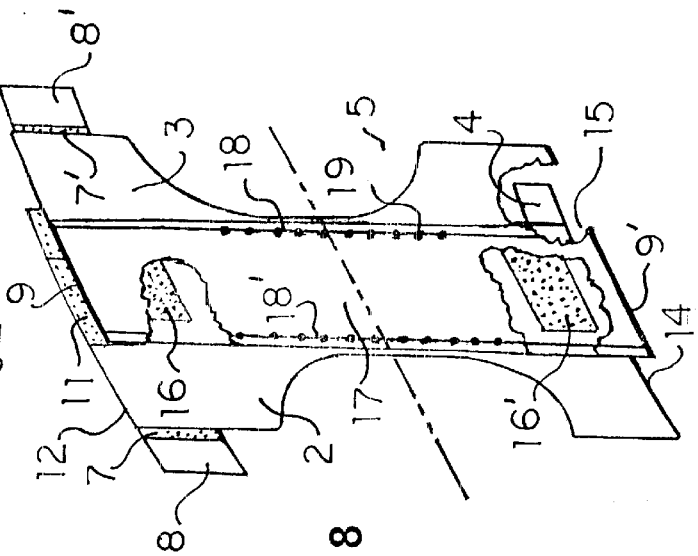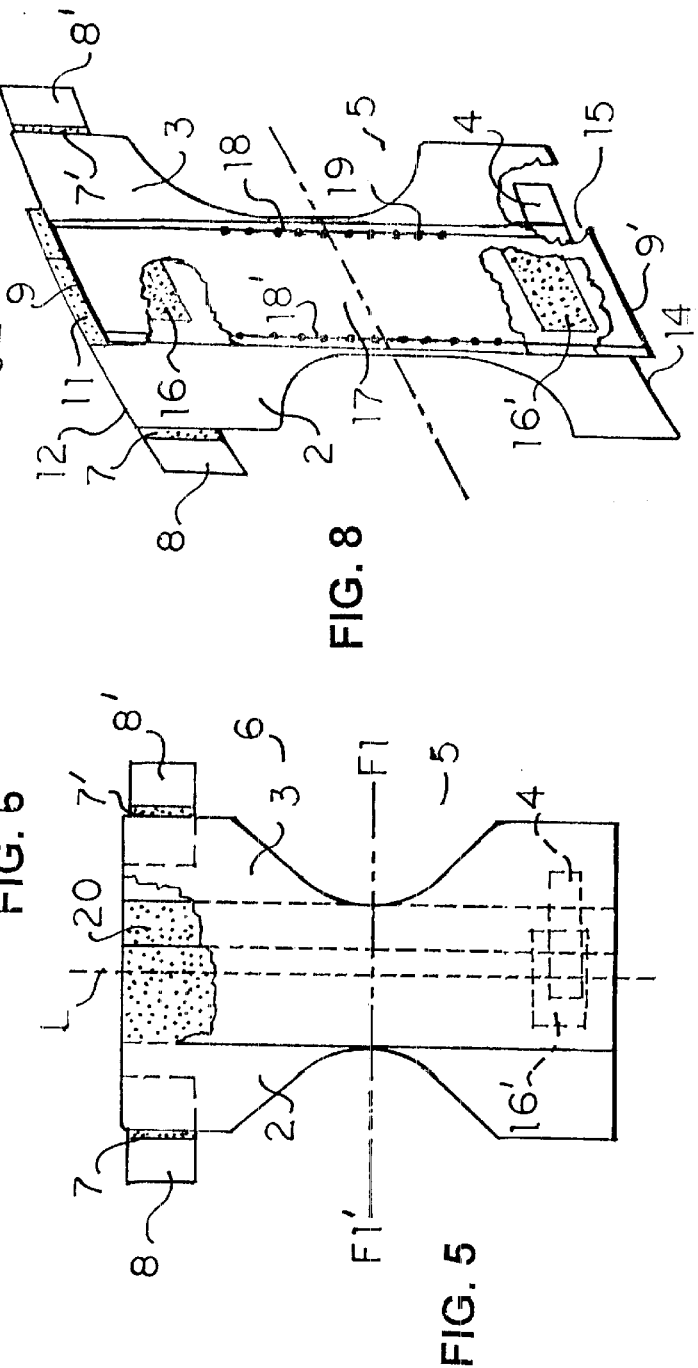

FRONT OPENING BRIEFS WITH INTEGRAL SUPPORT PANEL

BACKGROUND OF THE INVENTION

The present invention is a continuation-in-part of U.S. patent application 09/240,900 filed Jan. 29, 1999, now U.S. Pat. No. 6,092,242 issued Jul. 25, 2000.

U.S. Application '900 describes a brief assembly that is folded around a wearer's crotch, and after the user connects the front and rear panels with side margin tapes, it defines a folded hourglass-shaped undergarment constructed from two half width mirror image segments which are bonded together to from a unitary rear panel and left unbonded to define an opening in the front panel.

Class 604 contains many examples of disposable diapers applied to the user in a similar way.

In the instant invention, a front opening is constructed by longitudinally overlapping half width webs with the advantage that one or both of the overlapped marginal edges can be enclosed with folded strips that define a 'reinforced' front fly without further processing of materials except along longitudinal lines until the product is assembled and ready for separation into discreet units, thus the product is well adapted for high speed fabrication.

In co-owned U.S. Pat. Nos. 5,864,890 and 6,092,242, one embodiment of these previously described undergarments includes tensioned elastic strands to contract margins of the inner segment to form shirred cuffs and provide a seal against leakage.

Contraction of the elastic in the crotch region of '890 and '242 may cause minor undulations of the absorbent pad, although with certain open cell highly pervious materials, the gathering effects are minimal.

The tendency of attached pads to gather when the briefs of '890 or '242 are used with a pad for sanitary purposes is overcome in the instant invention by using an intergral support panel having elasticized side margins which form a pouch or pocket to hold body protuberances, and support/contain a separate absorbent pad of the user's choice.

With or without a pad, the longitudinally extended central area of the support panel remains substantially unaffected by contraction of the elastic.

For sanitary use, both male and female adults can attach absorbent pads of choice to the inner pad support panel.

In the present invention, the full front panel opening permits male urinary functions to be more readily achieved by allowing displacement of an absorbent pad to an offset position or the briefs may also be lowered to permits fund.

When the garment of the invention is used in combination with a pad, the combination describes a two-part system for fluid absorbency or waste containment.

During manufacture of the inventive garment, tensioned and stretched elastic strands are bonded to the side margins of a support panel at spaced intervals and the non-contracted full length support panel is bonded at opposite ends to the garment as described in related U.S. Pat. No. 6,250,357 B1.

When the web series of garments are fabricated and then cut into individual units (briefs), they are transversely folded for delivery and packaging with the result that elastic contraction causes the pad support segment to shirr along side margins.

The method of using the inventive briefs as an undergarment (without pad) comprises the step of applying the brief and connecting side tapes to complete waist and leg apertures. Concurrent contraction of the attached elastic forms the pocket or pouch for body protrusions.

The method of using the inventive briefs in combination with a separate pad to define a waste containment system comprises the steps of:
 a) stretching the overgarment (briefs) out flat,
 b) attaching an absorbent pad to an adhesive receptor area on the support panel and,
 c) folding the front panel around the crotch and attaching side tapes to connect front and rear panels.

SUMMARY OF THE INVENTION

The briefs of this invention are form y advancing two webs, each having a width equal to about one half the product width plus an amount of overlap in superposed partially overlapped relationship along a longitudinally extended zone.

Outer marginal portions of each web are removed for leg cutouts and, after selective bonding and attachment to each other, form an hourglass-shaped assembly of segments.

A selected portion of the overlapped region is bonded together so that equal and opposite segments form a unitary rear panel.

The non-bonded front panel portion of the overlap forms a 'fly' opening which allows the briefs to be opened when the user puts them on, or subsequently opens and closes the front panel.

A reclosable tape secures the openable front panel for use, and may remain closed for male urinary functions.

A third support panel segment having a width substantially equal to the width of the overlapped central area has tensioned elastic strands attached at spaced intervals that are secured to margins of the support panel segment which serves as a support surface for separate absorbent pads of the user's choice.

Accordingly, the object of this invention is to provide an undergarment brief having a support panel for body parts or a pad.

A further object is to provide a support panel with elasticized side margins to form a pocket or pouch with leg seals when applied to the wearer.

Another object is to provide a support panel having a cover strip protected adhesive area for attachment of a separate pad, for fluid absorption.

Other objects of the invention may be seen in the ensuing description.

BRIEF DESCRIPTION OF THE DRAWINGS

FIG. 1 is a perspective view of the undergarment illustrating the integral support panel with elasticized side margins.

FIG. 2 is a plan view of a half width segment illustrating the adhesive area that bonds two overlapped segments into a unitary rear panel.

FIG. 3 is a plan view of a second half width segment that is bonded to the segment in FIG. 2 to form the assembly illustrated in FIG. 6.

FIG. 4 is a plan view of the support panel looking at the inside surface that contacts the wearer illustrating spaced attachment of elastic strands along side margins.

FIG. 5 is a partially cut away plan view of the assembled segments of FIGS. 2, 3, and 4 illustrating the bonded rear panel, front panel opening, and attached support panel (elastic strands omitted for clarity).

FIG. 6 is a partially cut away plan view schematic of the manufacturing process illustrating sequential assembly of components with the innermost segment and pad support panel facing the viewer.

FIG. 7 is a cross sectional diagramatic view of assembled components taken along sight line 7—7 of FIG. 6 illustrating placement of components.

FIG. 8 is a partially cut away perspective view of the briefs illustrating the briefs with integral support panel including elastic on side margins.

DETAILED DESCRIPTION

In FIG. 1, undergarment briefs 1 are comprised of a first half width segment 2 and a second half width segment 3, each having a width substantially equal to about half the product width plus an amount for overlap.

In the manufacturing process (FIG. 6), first segment 2 (still in web form before being cut into discreet units) is advanced along a path.

Second segment 3 (still in web form) is superposed on top (see FIG. 6 for sequence and positioning) and advanced along the same path.

After certain fabricating steps described hereinafter, the two overlapped segments 2, 3 are connected with tape 4 (see FIG. 2) to form the front panel 5.

To use the product, front panel 5 is folded around the wearer's crotch section before side tapes 7,7' connect front and rear panels.

In FIG. 1, the overlap between opposing half width segments can be seen at 9 on the rear panel and 9' between segments of the front panel.

FIG. 1 shows briefs with an elasticized panel 17 (see also FIG. 4) for supporting body protuberances, noting that side margins of the panel contract to form a pouch or pocket as the briefs are put on.

FIG. 2 (seen from the inside) has a side margin tape 7 with detachable cover strip 8 bonded to the outside facing surface of segment 2.

Front panel connecting tape 4 protrudes beyond linear margin 10 of segment 2 and attaches segments 2 and 3 on surfaces facing outward as worn.

An area of adhesive 11 substantially the same width as the overlapped region between 9 and 9' extends from line F1–F1' to the waist margin 12 and bonds both half width segments 2, 3 in the overlapped central region to define the unitary rear panel.

It is within the scope of the invention that the adhesive area 11 can extend beyond F1–F1' to lower portions of what becomes the front panel (see 5 of FIG. 1).

In FIG. 2, central unbonded area 13 in the front panel between segments 2 and 3 extends from F1–F1' to the top margin 14 of front panel 5 and defines opening 15 (See FIGS. 1 and 8).

Without adhesive bonding between segments 2 and 3, flaps on the fly (not referenced for clarity) are held together with closure tape 4 near top margin 14 to facilitate later transverse folding of both segments as a unitary front panel.

The major portion of closure tape 4 is affixed to segment 2 and the free end extends over segment 3. For opening and subsequent reclosure, the free end can be attached to a release coated receptor area (4A in FIG. 7) on segment 3.

Each segment shown in FIGS. 2, 3, and 4 is assembled and superposed so that line L is coincident and positioned as in FIG. 5.

In FIG. 3, second segment 3 has side margin tape 7' affixed to the outside facing surface of the rear portion for use by the wearer to connect front and rear panels thereby completing waist and leg apertures as worn.

In FIG. 5, segment 3 is superposed over segment 2 with lines L of both segments arranged coincident to define the hourglass-shaped assembly of FIG. 1 before the support panel is secured to the inside surface of the innermost segment.

In FIG. 5, tape 4 attached to, and protruding from, segment 2 is attached to segment 3 across the unbonded overlapped flaps of the front panel opening 15 (see lower part of FIG. 8).

Referring back to FIG. 3, innermost segment 3 includes adhesive areas 16, 16' spaced a predetermined distance from fold line F1–F1' and from each other.

In the manufacturing process and sequence of component addition (see FIG. 6), adhesive in areas 16, 16' secure support panel 17 to the innermost half width segment 3 of the assembly shown in FIG. 6.

In FIG. 4, tensioned elastic strands 18, 18' are each bonded at spaced intervals 19A, . . . 19N, and secured to support panel 17 before it is bonded by spaced adhesive in areas 16, 16' to innermost segment 3.

In the 'free state' embodiment of FIG. 4, elastic strands 18, 18' are stretched and attached per the sequence of FIG. 6 and according to the methods of prior art, U.S. Pat. Nos. 3,828,367 and 4,081,301.

The tensioned elastic strands (in continuous form) are attached at spaced intervals to support panel 17 (in web form) which in turn is secured to spaced adhesive areas 16, 16' on the innermost segment 3 of the web assembly—these steps occurring while the elastic strands are in tension during advancement, noting that tension in the elastic strands caused by elongation creates the tendency to contract after cutoff and folding into unit assemblies.

In FIGS. 1, 2, 5, 6 and 7, a V-folded reinforcing strip 20 is adhesively bonded to both sides of segment 2. If preferred, the linear longitudinal margin of segment 3 can also be reinforced.

In FIG. 5, overlapped half width segments 2, 3 are assembled and attached with adhesive in area 11 and front panel connecting tape 4.

The assembly includes side margin tapes 7, 7' (support panel 17 and elastic strands are omitted for clarity ).

In FIG. 6, a first half width web 2 advances along a path, Second web 3 is offset and advanced in overlapping relationship with web 2.

An area of adhesive 11 on web 2 (or web 3) bonds the two half width webs together in the portion that becomes a full unitary rear panel.

Areas of adhesive 16, 16' are applied to the inside surface of the innermost segment 3 before a third segment 17 (also in web form) is added.

Third segment 17 (in web form) having stretched elastic strands along side margins is attached to segment 3 over adhesive areas 16, 16' and the web assembly is then cut into discreet units along lines C1–C1', C2–C2', etc., and side portions (not referenced for clarity) are removed to form the hourglass-shape.

In FIG. 6, elastic strands 18, 18' and attachment adhesive dots 19A . . . 19N, etc., are shown on the top inside surface of the support segment for illustration, however, the preferred location is between inside segment 3 and support segment 17 as shown in FIG. 7.

In FIG. 6, support segment 17 having a width substantially equal to the amount of overlap 9, 9' is affixed to adhesive areas 16, 16' and after cutting, is the same length as the brief assembly and extends from the front margin to the rear end margin as shown in FIGS. 6 and 8.

On the left side of FIG. 6, phantom areas 23, 23' are release coated receptor areas for temporary attachment of the side margin tapes 7, 7' after the garment has been folded for delivery from the manufacturing machine.

For product use, the tapes are detached from the temporary captive attachment areas on the front panel, the panel is folded around the user's torso, and tapes are reattached to the same receptor areas 23, 23' for wear.

In FIG. 7, the assembly is shown in cross section and viewed before cutoff. Segment 3 is reinforced along the right hand edge with V-folded strip 20. Side tapes 7, 7' are applied and covered with pieces 8, 8' on exposed adhesive areas.

Segments 2 and 3 are bonded together in the rear panel by adhesive in area 11.

Segment 17 has elastic strands 18, 18' attached along side margins and is bonded to the innermost surface in spaced adhesive areas 16, 16'.

Instead of tape, side margin fasteners 7, 7' and connecting tape 4 can be hook and loop grip fasteners having male protuberances that attach to female receptor areas. Tapes 4, 7, and 7' can have portions elasticized for stretch and tightness of fit around the wearer's waist.

Preferably the innermost segment of the superposed segments has an impervious material 3A bonded to its inside surface.

In FIG. 8, segment 17 extends from end margin 12 of rear panel 6 to end margin 14 of front panel 5 with elastic strands 18, 18' shown in a stretched mode but without optional pad or securement adhesive.

In FIG. 6 pad receptor adhesive areas 21 are applied for attachment of an absorbent pad P.

A removable piece 22 (see left side of FIG. 6) covers the pad receptor adhesive before use.

While in the foregoing specification a detailed description has been set forth for the purpose of illustration, many variations can be made in the details stated herein without departing from, or limiting, the spirit and scope of the invention.

It is within the scope of the invention to define other arrangements and embodiments according to the claims made hereinafter.

What is claimed is:

1. A garment comprising an inner pad support member superposed on, and bonded to spaced, adhesively coated, receptor areas on the inside of a rear panel portion and the inside of a front panel portion, respectively, said front panel portion also having a reclosable opening, said garment further comprising:

first and second shaped segments each having a length substantially equal to a distance between front and rear end margins of said garment, and first and second longitudinal side margins, said first and second segments partially superposed between said end margins along the first side margins to define a longitudinally extending overlapped area between said end margins, said first and second segments each having a width substantially equal to about half a width of the garment plus a width of the overlapped area, said first and second segments including curvilinear cut-outs along respective second longitudinal side margins, said rear panel portion including said first and second segments bonded together in a preselected portion of said overlapped area adjacent said rear end margin, said front panel portion opening defined by a non-bonded portion of the overlapped area adjacent said front end margin, said inner pad support member having a length equal to the distance between said end margins and a width substantially equal to the width of said overlapped area and further including:

stretched elastic strands adhesively attached at spaced intervals adjacent respective side margins of said support member, and central portions of opposite ends superposed on, and bonded to the adhesively coated, receptor areas of said rear panel portion and said front panel portion, respectively, fastening means protruding from both side margins of said rear panel portion for attachment to respective receptor areas on said front panel portion, and at least one central fastening means attached to an outermost surface of said front panel portion for reclosable securement of said first and second segments near the top of said front panel portion opening.

2. The garment of claim 1 wherein an adhesively coated pad receptor area is defined on an inside surface of said inner pad support member.

3. The garment of claim 2 wherein a release coated piece is applied over the adhesive of said pad receptor area.

4. The garment of claim 1 wherein said inner pad support member is a single ply of pervious material.

5. The garment of claim 1 wherein said fastening means receptor areas and said fastening means are spaced from respective end margins of said front and rear panel portions.

6. The garment of claim 1 wherein the longitudinal first side margin of at least one of said superposed segments is enclosed within a V-folded strip.

7. The garment of claim 1 wherein said superposed first and second segments are folded along a line which is not equidistant from front and rear panel portion end margins.

8. The garment of claim 1 wherein said preselected bonded area portion of said overlapped area extends to lower portions of the superposed segments of the front panel portion.

9. The garment of claim 1 wherein said central fastening means has at least one end with protuberances.

10. The garment of claim 1 wherein a portion of the side margin fastening means and the central fastening means is elastic.

11. The garment of claim 1 wherein said central fastening means is attached to a receptor area having a release coating.

12. The garment of claim 1 including an impervious material bonded to the inside surface of the innermost segment of the superposed segments.

* * * * *